United States Patent [19]

Bifuk

[11] Patent Number: 4,838,899
[45] Date of Patent: Jun. 13, 1989

[54] CURETTE SHARPENING HONE AND METHOD OF MAKING

[76] Inventor: Edward J. Bifuk, 1948 E. Kenwood Dr., St. Paul, Minn. 55117

[21] Appl. No.: 148,370

[22] Filed: Jan. 25, 1988

[51] Int. Cl.⁴ .............................................. B24D 3/00
[52] U.S. Cl. ...................................... 51/293; 51/204; 51/295; 51/298; 51/309
[58] Field of Search .................. 51/293, 295, 298, 309, 51/204

[56] References Cited

U.S. PATENT DOCUMENTS

| | | | |
|---|---|---|---|
| 1,976,070 | 10/1934 | Hermann | 51/280 |
| 2,278,442 | 4/1942 | Heaney | 51/309 |
| 2,290,877 | 7/1942 | Heaney | 51/309 |
| 2,404,192 | 7/1946 | Ries et al. | 51/211 |
| 3,248,189 | 4/1966 | Harris, Jr. | 51/295 |
| 3,394,502 | 7/1968 | Crowe | 51/204 |

Primary Examiner—Paul Lieberman
Assistant Examiner—Willie J. Thompson
Attorney, Agent, or Firm—Harold D. Jastram

[57] ABSTRACT

A dental curette hone consisting of a ceramic made from particulate aluminum oxide abrasive. The hone having a curved elongated edge and a flat elongated surface. The curved elongated edge having a radius of approximately 1/32 to about 3/32 inch. The ceramic block being made by forming a mixture of particulate aluminum oxide having an irregular particle shape and a selected particle size with magnesium oxide. Then shaping each block by extruding or molding. The block is then heated to form a fused ceramic block. The block is next tumbled to remove irregularities from the elongated edge and flat surface after which the block is polished to form a polished surface on exposed particles of aluminum oxide. The polished surfaces of said particles intersect irregular sides of said particles to form cutting edges on said particle for sharpening the curette.

37 Claims, 2 Drawing Sheets

CURETTE SHARPENING HONE AND METHOD OF MAKING

BACKGROUND

In the practice of dentistry and, in particular, periodontics, planing of the root surfaces of the teeth which have been exposed because of periodontitis (pyorrhea) is an important and necessary procedure in the treatment of every periodontal patient. The degree of success clinicians have with root planing is directly proportional to the success they will have treating periodontitis. It, therefore, behooves every clinician to do a meticulous job of root planing.

Whether root planing is performed with surgical access or in conjunction with other surgical procedures or without surgical access, sterile techniques must be stringently followed in maintaining the instruments used in such procedures. Like all other surgical instruments, they must be clean and sterile and maintained that way in a sterile field, throughout the root planing procedure. Sterile conditions must be maintained because instruments come in contact with the interstitial tissue and fluids of the periodontium and could introduce microorganisms or foreign bodies into the healthy tissues of the body.

The specific hand instruments, which are universally used, for root planing are the periodontal curettes. These instruments are made of stainless steel, so they will not rust or tarnish when they are subjected to cleaning and sterilization procedures. Instruments must stand up to autoclaving which exposes them to a temperature of 250 degrees F. at 18 pounds of vapor pressure per square inch for twenty minutes.

The two main objectives of root planing teeth (hard tissue curettage) are to remove all cementum and dentin which have been altered by the permeation of endotoxins and other toxic substances, and, second, to create a root surface which is hard and smooth.

In order to achieve the above goals in a meticulous manner, some degree of controlled penetration into the hard cementum or dentin is necessary. This controlled penetration can only be accomplished with curettes that are meticulously sharp and kept that way throughout the procedure. A dull instrument will not effectively remove the toxin-impregnated cementum or dentin and will not produce a smooth, hard surface.

A rough sharpened instrument will remove too much healthy cementum and dentin and not leave a smooth surface. A smooth surface is necessary for maintenance of plaque control. The rough tooth surface has a greater root surface per unit of area. A rough surface is difficult to maintain for plaque control.

Periodontal curettes become dull during the root planing procedure. In order to keep a sharp edge on the instruments during root planing, without contaminating them, a sterile sharpening device must be kept in the sterile pack, along with the sterile instruments.

When periodontal instruments are sharpened, the steel surface is drawn across a stone and bits of metal are abraded away. Serrations are formed on the surface of the instrument. Serrations on two intersecting surfaces of a curette form points on the cutting edge. An objective in sharpening a curette is to minimize the depth of the serrations on the intersecting surfaces, to minimize the size of the points formed on the cutting edge. For best results, the serrations (ridges and gullies) should run parallel to each other and perpendicular to the cutting edge. The serrations on one of the surfaces should not run parallel to the cutting edge, because this weakens the edge. For maximum strength of the edge, the base should not be decreased in order to maintain the base to point ratio. When the base is reduced, the points break off easier and further down the base. This means a duller instrument faster. A more desirable objective is to sharpen the curette with no formation of serrations or with serrations which have very shallow gullies.

The results obtained while sharpening instruments depend upon the compatibility of the characteristics of the sharpening stone with the type of metal alloy in the instrument. The alloys used in periodontal instruments are all about the same composition. The metal is stainless steel. Conventional sharpening stones, commonly used in root planing, are made up of abrasive particles which do the abrading and a bonding agent that holds the abrasive particles together. The characteristics of conventional sharpening stones depend on:

(1) Type and hardness of the abrasive particle.
(2) Size, shape and uniformity of the abrasive particle.
(3) Height of the abrasive particle above the bonding agent on the surface of the stone.
(4) The distance between the abrasive particles on the surface of the stone.
(5) The firmness of the bonding agent holding the abrasive particles together.

Varying these different characteristics in a stone will modify the results produced in the sharpening process. For example, stones with small-size abrasive particles spaced close together will produce smaller serrations than stones of the same abrasive particle size whose abrasive particles are spaced farther apart. Sharpening stones with the abrasive particles closer together will generate far more heat from friction, and it follows that less heat is generated when the abrasive particles are spaced farther apart. This is one of the reasons, even with a coolant, mechanical sharpeners cannot produce a meticulously sharp edge without overheating the metal in the instrument. This overheating removes the temper from the metal and, with it, its ability to hold a edge.

Conventional sharpening stones with weaker bonding agents give up the abrasive particles freely in order to abrade to less serration depth and less heat from friction, but these stones require a lubricant. The lubricant acts as a vehicle for the abrasive particles to come to the surface of the stone, not to make the abrasive particle slippery to reduce abrasion, thus friction. It is the abrasion that does the sharpening. If a lubricant is not used with these types of stones, deeper serrations in the metal surface will result.

Sharpening stones are either man-made or found in nature. The common man-made stones used in periodontics have either aluminum oxide or silicone carbide as the abrasive particle. These abrasive particles are used in different grit sizes and in different concentrations, with different types of bonding agents. The stone found in nature, commonly used in dentistry, has naviculite as the abrasive particle. This is the Arkansas stone.

None of the sharpening stones commonly used to sharpen periodontal instruments were designed and manufactured specifically for periodontal instruments. These are some of the problems with these conventional stones:

(1) None of the stones will produce a meticulously sharp edge (an edge produced by surfaces that do not show their serration under a ten power eye loupe).

(2) The Arkansas stone will produce a fairly good edge, but a lubricant must be used. Abrasive particles are given up in the sharpening process which grooves and valleys on the sharpening surface. The Arkansas stone is porous and difficult to scrub clean and will not hold up during sterilization in the autoclave.

(3) Some stones that will hold up under autoclaving are far too rough for good results. The stones usually need a lubricant and they usually give up abrasive particles during sharpening. The giving up of abrasive particles not only causes grooves on the surface of the stone but the particles given up can mistakenly be transferred to the periodontium as a foreign body. Such foreign bodies can cause a foreign body reaction by the patient.

(4) Common stones all remove too much metal from the instrument in the sharpening process and, therefore, reduce the life of the instrument.

When sharpening with the coarse conventional stones, the curettes end up with a cutting edge made up of large points, that is in essence a rake. When such a working edge is tested on a fingernail, it grabs and this is mistaken for being sharp. This rake edge produces a rough surface on the root of the tooth and too much good tooth structure is removed. When the curette is used to root plane, the metal points break off because the points lack support from the base. This rake edge lacks cutting ability, it must tear through the cementum and dentin leaving a rough surface. This dullness becomes aggravated with use. Each of the non-cutting, broken points becomes a stress point. The shock on the points being advanced through cementum and dentin, tends to break off the points further down towards the base, thus breaking down the edge still further. This means the rake edge breaks down faster and farther and requires that much more metal be removed in order to resharpen the curette. Also the sharpening must be repeated more often.

Consequently, coarse stones reduce the life of the instrument. This is why a meticulously fine edge, maintained on a instrument during root planing, increases the life of the instrument.

Clinicians typically believe that the curettes they purchase new, come from the manufacturer properly sharpened for root planing. One can almost see with the naked eye (more dramatically observed with a jewelers loupe), that two things are wrong with the blade of the instrument. First, there are deep serrations on the face and side of the instrument that forms the working edge. Second, the serrations on the face of the instrument run parallel or nearly parallel to the working edge. The reasons for such serrations are that the curettes were sharpened at the factory with a mechanical sharpener. Even though manufacturers use a coolant, they have to use a coarse stone with the abrasive particles spaced far apart or they will overheat the metal during sharpening and all the temper of the steel will be lost and, with it, the ability to hold a sharp edge.

Further, mechanical grinding wheels cannot sharpen the face of a curette in a direction perpendicular to the cutting edge. Consequently, a clinician must spend substantial time sharpening a new instrument and correcting these defects.

Clinicians have had to accept the difficulty of working with instruments that have been sharpened with a coarse stone. The roughness in the cutting edge of the instrument is replicated on the root surface during the root planing procedure, thus a rough surface is produced. With the rake edge, the cutting edge removes an excess of good sound tooth structure. Also, with a rake edge, more hand pressure on the instrument is required, and more time is needed to root plan the teeth. This means a clinician has less tactile sense and requires more time with more trauma to the patient.

BRIEF DESCRIPTION OF INVENTION

It is, therefore, an object of this invention to provide a hone for sharpening dental instruments where the hone is made from a ceramic material designed specifically for sharpening curettes used for meticulous root planing.

Another object of the present invention is to provide a hone for sharpening dental instruments in which the hone is composed of a high fusing, solid state, high purity, fine grained, dense and impervious ceramic sharpening abrasive with the hone having an elongated edge which is rounded to accommodate the curved surfaces of dental instruments having curved cutting edges.

Another object of the present invention is to provide a hone for sharpening dental instruments having curved cutting surfaces in which the hone is composed of a fused particulate abrasive which is capable of withstanding autoclave sterilization temperatures and ultrasonic cleaning procedures and which requires no lubricating fluid for sharpening purposes.

Another object of the present invention is to provide a hone for sharpening dental curettes having curved cutting edges utilizing particulate aluminum oxide fused to form a ceramic capable of withstanding autoclave temperatures and to provide curved surfaces on a block of the ceramic hone where the curved or rounded surface has a radius of curvature of about 1/32 inch to about 3/32 inch for accommodating the curved cutting edge of the curette.

A further object of the present invention is to provide a hone for sharpening curettes where the hone is constructed of a fused particulate abrasive material capable of withstanding autoclaving sterilization temperatures and vapor pressure in which the particulate abrasive material makes up at least 83% of the composition of the hone.

A further object of the present invention is to provide a hone for sharpening dental curettes and other instruments having curved cutting surfaces where the hone is composed of a particulate abrasive material having a particle size range of approximately 0.5 microns to 8.5 microns and where exposed particles have polished surfaces for sharpening a curette.

Another object of the present invention is to provide a hone for sharpening curettes where the hone is composed of particulate aluminum oxide and magnesium oxide in which the irregular-shaped particles of the aluminum oxide are polished where the particles are exposed at a surface of the hone to provide sharp cutting edges at the intersection of a polished surface of the particle and irregular sides of the exposed particles to provide a sharp cutting edge on said particle for sharpening the curette.

Another object of the present invention is to provide a hone for sharpening curettes where the hone is composed of particulate aluminum oxide and magnesium oxide in which irregular shaped particles of the aluminum oxide are polished where the particles are exposed at the surface of the hone to provide sharp cutting edges at the intersection of a polished surface of the particle and the irregular size of the exposed particles to provide a sharp cutting edge which produces the smooth surface honing results as if the abrasive particles were extremely small and retains the rapid abrading advantages of the larger abrasive particles in the hone for the purpose of sharpening dental curettes.

Another object of the present invention is to provide a hone for sharpening curettes where the hone is composed of particulate aluminum oxide and magnesium oxide in which irregular shaped particles of the aluminum oxide are polished where the particles are exposed at the surface of the hone and provide sharp cutting edges at the intersection of a polished surface of the particle and the irregular sides of the exposed particle to provide a sharp cutting edge. Further, the exposed particles are not worn down and are not given up from the surface of the hone when the hone is used for the purpose of sharpening dental curettes.

A method is contemplated for making a hone for sharpening a curette having a curved cutting edge where an abrasive in particulate form is combined with magnesium oxide and the mixture is then formed into an elongated block having an elongated flat surface and one rounded or curved edge with a radius of curvature of about 1/32 inch to 3/32 inch and is capable of accommodating the curved surface of a curette. The formed block is heated to a fusing temperature to fuse the abrasive to form a hone capable of withstanding pressure and temperature conditions in an autoclave. Particles of abrasive exposed at the honing surface of the hone are polished to form a cutting edge on each exposed particle with the cutting edge being formed at the intersection of the polished surface and the side of the particle.

A method according to the present invention contemplates selecting a particulate aluminum oxide in which the particles are of irregular shape as the abrasive material to be used in forming a hone. The aluminum oxide particles are then mixed with magnesium oxide after which the mixture is formed into an elongated block having an elongated flat surface and one elongated rounded edge where the radius of curvature of the edge is about 1/32 to about 3/32 inch and capable of accommodating the curved cutting edge of a curette. The shaped hone is then subjected to fusing temperatures to fuse the particulate aluminum oxide particles to form an impervious, high purity, fine grain, dense, solid state ceramic hone. The hone is then tumbled in a tumbling compound to remove any surface imperfections from the shaping step. The flat surface and rounded edge surface of the hone are then polished to produce a flat polished surface on the particles of aluminum oxide exposed at the flat surface and rounded surfaces to produce a cutting edge on the particles at the intersection of the polished surface and irregular side of the particulate aluminum oxide. A final step might include bonding two blocks of ceramic having differing coarsenesses together with a bonding agent such as a thermal setting epoxy in order to provide a hone having two grades of coarseness to sharpen the cutting edges of curettes.

DRAWINGS

FIG. 1 of the drawings is a perspective view of a hone having a rectangular shape according to the present invention showing a hone composed of two blocks of differing coarseness with curved surfaces adapted to accommodate curved cutting surfaces of dental instruments.

DETAILED DESCRIPTION OF INVENTION

Figure 1:
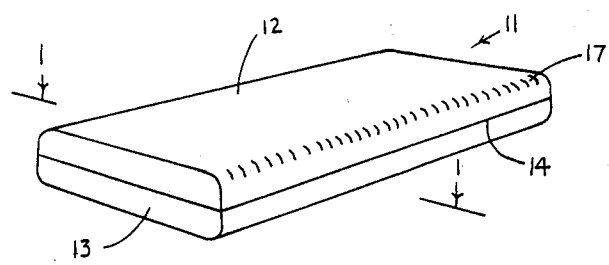
Figure 1A:
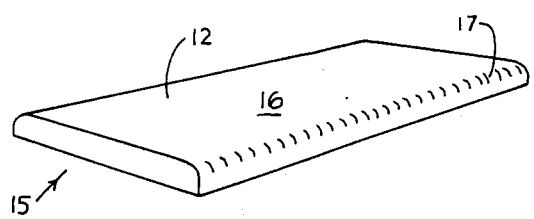

Refer first to FIG. 1 of the drawings which illustrates a hone generally designated by numeral 11. Hone 11 is composed of two blocks, 12 and 13, which are bonded at joint 14 by a bonding or adhesive agent. FIG. 1a illustrates a hone according to the present invention where only a single block 12 is used.

Figure 3:
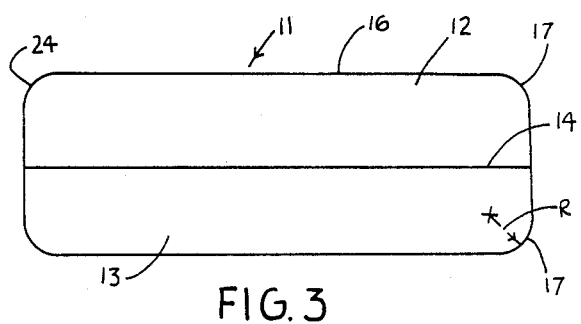
FIG. 3 is a cross-sectional view taken along line 1—1 of FIG. 1 of the drawings showing the rectangular cross-sectional shape of the hone illustrated in FIG. 1 of the drawings.

Each block 12 and 13 in a preferred embodiment of the invention has essentially a rectangular cross-section as illustrated in FIG. 3 of the drawings. While a rectangular cross-section is preferred for the cross-sectional area of the hone 11, the blocks 12 and 13 could also be formed so that the final cross-sectional shape of the hone 11 is essentially a square. A rectangular cross-sectional area, however, is a preferred shape since this particular shape provides a flat elongated surface 16. Elongated surface 16 provides a relatively large flat surface capable of engaging a dental instrument to be sharpened.

Elongated curved or rounded edge 17 provides a very special and highly important feature of the present invention. Elongated edge 17 provides the curved abrasive surface which is specifically adaptable to engage the curved cutting edges and surfaces of dental curettes for the purpose of applying a sharp, smooth cutting edge to these dental instruments.

Figure 6:
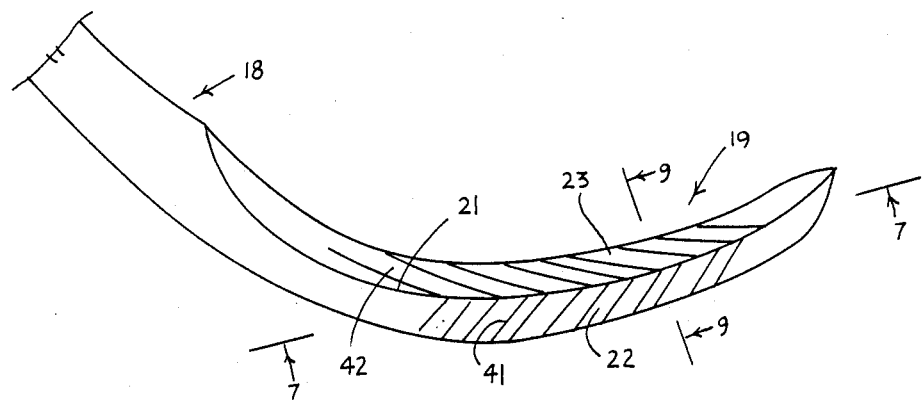
FIG. 6 is an enlarged view of a dental curette showing only the cutting edge and part of the handle.
Figure 9:
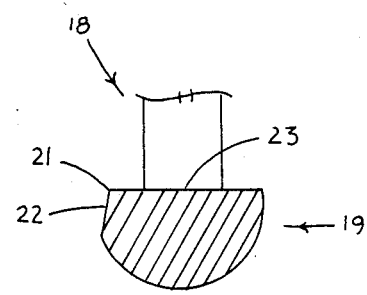
FIG. 9 is a cross-sectional view taken along line 9—9 of FIG. 6 showing cutting edges of a curette.

An illustration of the type of edge which is to be sharpened by the hone 11 and which is the subject of this invention is illustrated in FIG. 6 of the drawings. A curette generally designated by the numeral 18 is illustrated in fractional view. The curette 18 shows only the working section generally designated by numeral 19. The working section 19 has a cutting edge 21 which is sharpened by honing side surface 22 and face surface 23 using a sharpening stone or hone such as hone 11. FIG. 9 of the drawings also illustrates the relationship of the surfaces 22 and 23 to the cutting edge 21.

Figure 10:
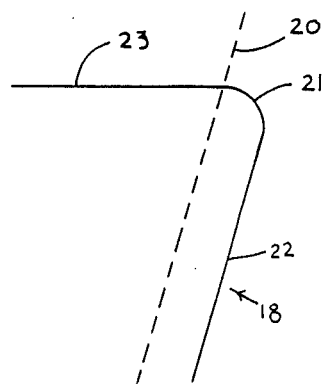
FIG. 10 is a fractional view of a dull edge of a curette.
Figure 10A:
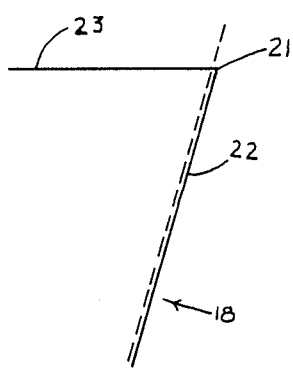
FIG. 10a is a fractional view of a sharp edge of a curette.

Reference to FIGS. 10 and 10a of the drawings will reveal the relationship of cutting edge 21 to surfaces 22 and 23 of the curette 18. FIG. 10a is a greatly enlarged view showing the cutting edge 21 in its preferred sharpened condition which is formed by the intersection of surfaces 22 and 23 of the curette 18. Hone 11, as will be hereinafter further explained, is used on both the side surface 22 and the face surface 23. FIG. 10 of the drawings illustrates a curette 18 which has a rounded and therefore dull edge 21 which needs to be sharpened. Sharpening may be achieved by removing metal from side 22 so that edge 21 will coincide with line 20 and thereby move the sharpened edge 21 to the intersection of face 23 and side surface 22. If edge 21 is as rounded as it appears in FIG. 10 of the drawings, the curette will not function properly and will not effectively carry out the curettage procedure desired by the dental clinician. It is under these conditions that the curette 18 will need to be sharpened by the clinician to restore the edge to one which has a sharp intersection illustrated by FIG. 10a of the drawings.

Specific attention is directed to the fact that curette 18 has a cutting edge 21 which is curved. This curved edge 21 is formed by the curvature of the working portion 19 of the curette and is typical of many cutting instruments used in the dental profession. The curved edge is of a particular size and shape for a very specific reason. The dental curettes are specifically designed to treat the curved surface of teeth, including, especially, the root surface of teeth below the gums.

Human teeth have through years of evolution developed so that most teeth are of generally the same general size and shape. This generally uniform size and shape characteristic of human teeth includes a certain roundness of the tooth surfaces, including the roots which fall within relatively specific size ranges. Experience has taught that curettes and other dental implements which are most successfully designed for use in dental applications should have cutting edges 21 which are curved at a specific radius of curvature.

Effective removal of cementum from the root surface of a tooth without damage to the soft tissue surrounding the tooth, therefore, has dictated the development of a curved edge 21 which can accommodate the curvature of the tooth as closely as possible. This cutting edge 21 must be sharpened and kept sharp to provide effective removal of the cementum and other deposits. Without employing a sharp edge 21 which is also of a relatively uniform and specific curvature, the practitioner removing the cementum may merely burnish the surface of the tooth without actually removing the unhealthy cementum. This results in a poorly treated tooth surface, with the effect that proper treatment of the periodontal problems is not effectively accomplished.

Further, the edge 21 must be curved so that the clinician can rotate the curette during the procedure to match the curved cutting edge 21 to the tooth surface and thereby avoid damaging the gum surrounding the tooth. While teeth are of a generally uniform shape, they individually have many variations which demand a curved cutting edge 21 of the type developed for curettes. Care must be exercised so that the cutting procedure does not cause damage to the gums surrounding such teeth.

Because of the precise needs for producing a very sharp edge 21 on a curved curette 18 or similar dental instrument, a hone 11 must contain curved surfaces which can be employed to place a sharp, smooth edge 21 on the curette 18. It has been discovered that the curvature for a hone surface which can best be employed to place a sharp edge 21 on a curette 18 falls within a relatively precise curvature which is illustrated in FIG. 3 of the drawings. The rounded elongated edge 17 with a radius falling in the range of 1/32 inch to about 3/32 inch in radius depicted by radius R is most effective in applying a smooth cutting edge 21 to curette 18. Radius R can be varied within the relatively narrow limits of 1/32 of an inch to about 3/32 of an inch in order to accommodate curettes 18 with slightly different curved edges 21. It has been learned, however, that the optimum radius R for curved elongated edge 17 is an edge 17 which has a radius R of 1/16 inch.

Elongated edge 17 can be placed along only one edge of block 12 and along only one edge of block 13. An alternate embodiment might employ two rounded edges 17 and 24 as illustrated in FIG. 3 of the drawings. The elongated edges 17 and 24 are formed on the block 12 during manufacture of the block 12 and which will be more fully explained hereinafter. A single block 12 illustrated in FIG. 1a of the drawings provides a satisfactory hone 15 with surface 16 of a single coarseness. If more than one coarseness of stone is desired, then a multiple block hone like that in FIG. 1 might be employed. Two blocks of essentially the same cross-sectional shape such as illustrated by blocks 12 and 13 can be bonded by an adhesive of proper choice along a joint 14 with the rounded edges 17 and 24 out of contact with the joint 14 to make a hone of two grades of coarseness.

Figure 2:
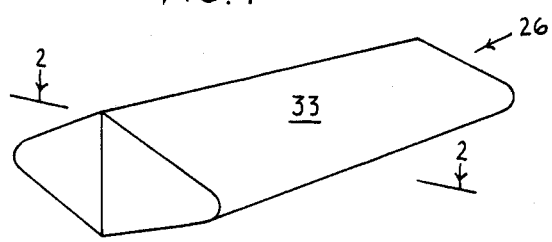
FIG. 2 is a perspective view of a hone composed of two blocks of material and with each block having essentially a triangular cross-sectional shape with a curved surface adapted to accommodate curved cutting surfaces of dental instruments.
Figure 4:
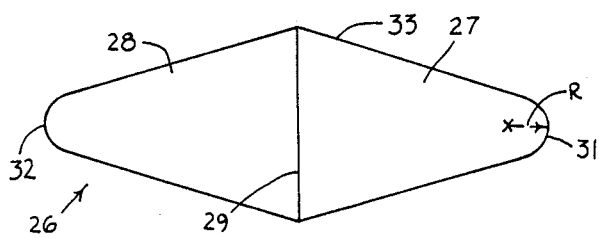
FIG. 4 is a cross-section of FIG. 2 taken along line 2—2 of FIG. 2 showing a hone composed of two blocks having an essentially triangular cross-sectional shape.

Another hone of different cross-sectional shape is illustrated in FIG. 2 of the drawings and is designated as hone 26. Hone 26 is composed of two blocks 27 and 28 which are joined along joint 29. The cross-sectional shape of hone 26 is illustrated in FIG. 4 of the drawings where it is apparent that each block 27 and 28 has essentially a triangular shape with a rounded elongated edge at one juncture of the legs of the triangular shape and which forms each of the blocks 27. In the case of hone 26, each block 27 and 28 is joined along joint 29 by an appropriate adhesive so that rounded elongated edges 31 and 32 are again out of contact with the joint 29 and in the case of hone 26 are at opposite extremes of the sides of the hone 26. As with hone 11, the elongated rounded edges 31 and 32 have a radius R of curvature which is from approximately 1/32 inch to approximately 3/32 inch. Again, however, it has been discovered that the optimum radius of curvature R for each of the edges 31 and 32 is a radius of 1/16 inch. As with hones 11 and 15, hone 26 also has elongated flat surfaces 33 which cooperate with elongated edges 31 to provide surfaces which may be utilized by a dental practitioner to effectively sharpen the cutting edge 21 of curettes and other dental implements.

Another indispensable attribute of a hone adapted to function in the unique and specific environment of the dental office is the need for the hone to be sturdy enough to withstand many repetitions of cleaning and sterilization in ultrasonic cleaners and in autoclaves. The need to withstand ultrasonic cleaning and autoclave procedures is important to a dental office since the dental instruments must be repeatedly cleaned and sterilized using one or more of the indicated methods. Mere cleansing and sterilization of the cutting implement is not satisfactory. The hone which is used while treating a patient must also be clean and sterile. When curettes are sharpened during a planing procedure or at the end of the procedure, the hone will tend to pick up contamination in the form of cementum, dentine, food particles from around the teeth and metal from the curette. Further, any bacteria accompanying this contamination or blood and saliva may become deposited on the hone. All of these contaminants must be removed from the hone. Consequently, frequent sterilization and cleaning of the hone is as important as cleaning and sterilization of the dental cutting implements. Proper maintenance of the implements in the dental office then requires frequent autoclave sterilization and ultrasonic cleaning of not only the cutting instruments themselves but also the hone which is used to maintain those instruments. Therefore, it is desirable to have a hone which can withstand the cleaning action that takes place in an ultrasonic cleaner and the temperature and pressure levels experienced in autoclave sterilization procedures in the dental office and still produce a meticulously sharp edge on an instrument. The hone made according to the present invention will withstand these cleaning and sterilizing procedures and also produce a fine edge on an instrument as will be hereinafter explained.

The natural stones, such as the Arkansas stone used in some dental offices do not produce a meticulously sharp edge. They require lubrication with a lubricating oil for proper functioning of the stones. These lubricating oils are difficult to use in a sterile field. Added work is necessary to remove the lubricating oil each time it is to be cleaned and sterilized.

A further problem encountered through the use of the Arkansas stone is the tendency of the stone to deteriorate and break down when it is subjected to the repeated temperatures and pressure conditions present in the autoclaving procedure.

Certain stones used in dental offices also have a tendency to give up abrasive particles from the surface during the sharpening process with the result that the abrasive surface will become grooved. When the abrasive surface becomes grooved, it also becomes uneven and the effective sharpening capabilities of the stone will be reduced. Further, these abrasive particles given up by these stones will tend to become contaminants which could cause inflammation or other problems if the particles are carried from the sharpening stone to the patient's mouth if the curette is sharpened during the planing procedure. The hone made according to the present invention does not give up these surface particles because the hone is constructed of a strong, hard, impervious, abrasive material which is composed of aluminum oxide particles of irregular shape fused to form an impervious block 12. Such a fused impervious block can be subjected to repeated treatment at high temperatures and pressures and to the cleaning action of an ultrasonic treatment device without causing the stone to breakdown.

Figure 5:
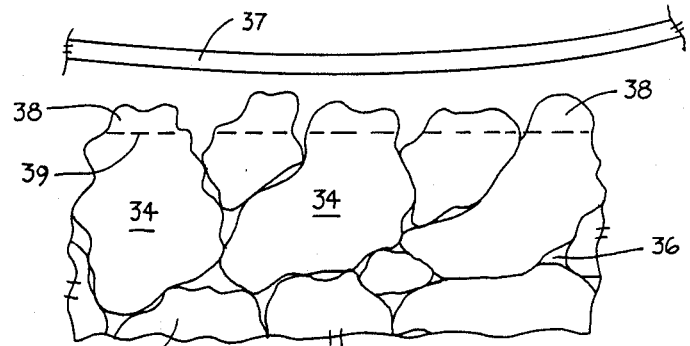
FIG. 5 is an enlarged fractional view of a hone in accordance with FIG. 1 of the drawings in which particulate abrasive is fused to form an impervious material.
Figure 5A:
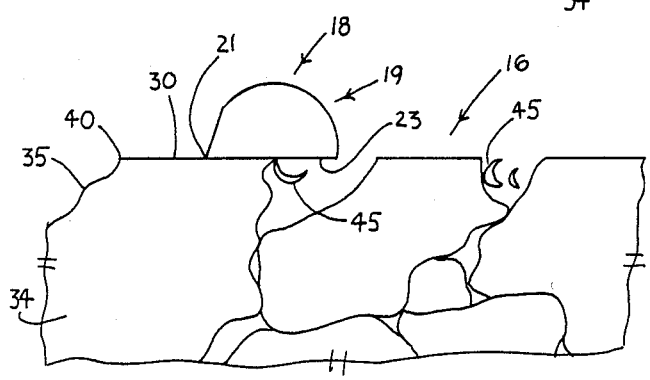
FIG. 5a is an enlarged fractional view of a hone in accordance with FIG. 1 in which a curette is being sharpened by polished particulate abrasive particles.

The hone is a mixture of aluminum oxide and magnesium oxide. The aluminum oxide in particulate form with the particles having an irregular shape as illustrated in FIGS. 5 and 5a of the drawings is selected as the abrasive and is present in the mixture at a level of over 83%.

To this mixture, magnesium oxide is added in very small and not critical concentrations. In a hone having 99.9% aluminum oxide, the remaining 0.1% will be magnesium oxide. The magnesium oxide is added in order to prevent the aluminum oxide particles from becoming larger or "growing" when the entire mixture is subjected to fusing temperatures in a kiln or similar heating device. It is desirable that the particle size for the aluminum oxide be maintained in the range of 0.5 to about 8.5 microns in size in order to preserve the characteristics of the finished ceramic hone necessary for effective sharpening of curettes. The magnesium oxide acts as a crystal growth inhibiting agent which will prevent the individual particles of aluminum oxide from growing to larger particles than the indicated range during this baking or fusing process.

Densifying agents may also be added to the ceramic employing the lower percentage of aluminum oxide. These densifying agents are taken from the group consisting primarily of silicon oxide, ferrous oxide, sodium oxide, chromium oxide, potassium oxide, phosphorus oxide, barium oxide and calcium oxide. These densifying agents 36 tend to fill any small spaces which may exist between the individual particles 34 of aluminum oxide and thereby promote the production of a ceramic hone which is extremely impervious.

While the concentration of aluminum oxide particles in the mixture is at least 83%, it has been found that a very effective hone can be made from a mixture which contains from 96% to 99.9% aluminum oxide particles with the remainder of the mixture composed of magnesium oxide and one or more of the indicated densifying agents. An important attribute of the inventive features of this hone is that a hone of fine quality capable of sharpening a curette with production of very few serrations can be achieved according to this invention even if the presence of aluminum oxide particles varies over a wide range. This attribute of the present invention which permits this to be accomplished involves the polishing of a surface of the particle 34 which is exposed at the elongated flat surface 16 and elongated rounded edge 17 of the hone.

Aluminum oxide has been found to be an effective and the preferred abrasive material to form the abrasive part of the hone. The aluminum oxide is in a particle form, with the particles of irregular shape. A preferred particle size for these abrasive materials has been found to be approximately 0.5 to about 8.5 microns in particle size.

The mixture of particulate aluminum oxide abrasive and magnesium oxide and the densifying agent, if used, is then formed into blocks characterized by blocks 12, 13 and 33 by either extruding the material or molding the material into the indicated shapes. The mixture is subjected to high pressures typical of extrusion and molding processes, with the result that a block of the mixture is dense and compact. Such a compacted block will hold together without further processing, but it is not strong enough to meet the needs of the present invention.

The length of the individual blocks 12 and 27 to produce elongated surfaces 16 and 33 can be a matter of choice. The blocks only need to be sufficiently long to provide a conveniently useful length for sharpening dental cutting instruments. The length of the finished hone 11 must be easy to handle. Lengths of about 4 inches have been found to be convenient although not critical.

After the blocks are extruded or molded to the proper shape as indicated in the drawings, the molded mixture is baked in a kiln where it is subjected to temperatures of about 1450 degrees Centigrade to about 1750 degrees Centigrade for a sufficient period of time to cause the aluminum oxide particles to fuse. As previously explained, the magnesium oxide prevents crystal growth of the aluminum oxide particles during this heating step to preserve the particles necessary to this invention. It has been found that the fused aluminum oxide forms a ceramic sufficiently strong and durable that it is capable of withstanding repeated ultrasonic cleaning and autoclaving sterilization procedures without damage to either the surface of the hone or the structure of the stone. The fused aluminum oxide is impervious, strong and hard. It will not give up particles from the surface 16 or 17 of the hone when a curette is sharpened and the aluminum oxide particles will not wear down when used to sharpen dental curettes.

Refer now to FIG. 5 of the drawings which is an illustration of a section of a hone showing the fused abrasive particles 34 and densifying agent 36. FIG. 5 is a greatly enlarged graphic illustration of the structure that exists throughout the hone 11 and which also depicts a greatly enlarged cross-sectional view of a surface of hone 11

An important attribute of the present invention which distinguishes it from other hone in the prior art involves the treatment of the surface of the hone which is exposed to the curette 18 as the curette is being sharpened. The specific treatment of elongated flat surface 16 and curved or rounded elongated edge 17 are of particular importance in the attributes of the hone according to this invention and the process for making such a hone.

Refer now to FIG. 5 of the drawings where particles 34 are illustrated in a fused condition. In the typical hone employing particulate abrasive materials, the hone will have irregular particles similar to particles 34 exposed at the surface of the hone. These exposed particles 34 have tops 38 which are of irregular size and shape and in the typical stone are the surfaces which cut the steel of a curette when it is being sharpened. It has been found that these irregular shapes with top 38 are the features which produce deep serrations in the surfaces 22 and 23 of a curette illustrated by serrations 41 and 42. To obtain a cutting surface or honing surface 16 and edge 17 which produces a much finer quality edge 21 on a curette 18, it has been found that the tops 38 of particles 34 must be polished. This polishing of the tops 38 of particle 34 achieves the high abrasive cutting action typical of large particles but also realizes the advantages similar to a fine honing characteristic normally found only in a very fine particle size which has very little abrasive action.

Figure 5B:
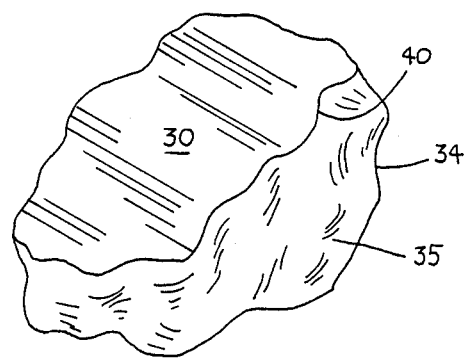
FIG. 5b is a perspective view of a single particle of abrasive material illustrating a polished surface to form a cutting edge on the particle.

Polishing, coupled with the characteristics that hone 11 does not give up its abrasive particles at the surface and that the abrasive particles are not worn down at the surface when curettes are sharpened, are important aspects of this invention. Abrasive particles are not worn down at the surface when curettes are sharpened and the tops 38 of particles 34 are polished to produce a flat area 30 on the top of particles 34. This flat area 30 is illustrated in FIG. 5b of the drawings and is illustrated as line 39 in FIG. 5 of the drawings.

This flat polished surface 30 is placed on the tops 38 of the particles 34 by polishing the surface 30. Polishing of the particles 34 can be accomplished through a wide variety of polishing techniques. Examples of these polishing techniques are the use of a polishing wheel, polishing belts, a polishing lathe and other polish grinding techniques. The polishing compound employed in these techniques need only be a material which is harder than the aluminum oxide or the abrasive that is being used to form the ceramic hone. A preferred method of accomplishing this polishing step is to utilize diamond to cut the tops 38 from the particles 34. This polishing or cutting step effectively produces a flat surface 30 which intersects with the irregular side 35 of particle 34. The intersection of flat surface 30 with irregular side 35 produces a cutting edge 40 along the entire surface of the polished surface 30. Consequently, each particle 34 has a polished surface 30 with an elongated irregular cutting edge 40. This cutting edge 40 is the feature which uniquely characterizes the present invention.

Cutting edge 40 is present on each particle 34 and is a much more uniform cutting feature than the ragged irregular top 38 of particle 34 than characterizes prior art hones. During the polishing action, very little material needs to be moved from the top 38 of the particle 34 in order to achieve the features of this invention. Only enough material needs to be removed from the top 38 of the particle in order to provide the cutting edges 40 which are employed to form a hone which preserves the advantages of large particle size cutting action and yet achieves the advantages of the effects of extremely small size abrasive particles.

A reference to FIG. 5a of the drawings will reveal the unique characteristics and uses of the polished surface 30 and edge 40 as a curette working section 19 is moved across a flat surface 16 of hone block 12. As the working section 19 is moved across the flat section 16, the sharp cutting edge 40 of each of the particles 34 will act as a plane which will evenly slice a small sliver 45 of metal from the surface 23 of the curette in order to perform the sharpening action to sharpen edge 21 of the curette 18. The important characteristic of polished surface 30 is that the intersection of that polished surface 30 with irregular side 35 produce an extended cutting edge 40 which engages the curette surface 23 to remove minute slivers of metal 45 without producing deep serrations. These small slivers are more typical of the filing removed by hones employing very small particle size which do not have a good abrasive action.

At this point it will be apparent that an additional important attribute is realized from the present invention. Refer to FIG. 5a of the drawings. Metal sliver 45 is removed from the surface 23 of the curette 18. This sliver 45 in a typical stone, which will not place a meticulous edge on the curette, will clog the surface of a typical stone if oil is not used. This is frequently referred to as metal fouling. Frequently, this metal fouling will stay on a typical stone and will often either result in a failure to sharpen the curette if oil is not used, and if oil is used the metal particles may be transferred to the patient's mouth where they will become a foreign body which may cause a negative reaction in the patient. If these metal particles are allowed to remain on the stone, they are very difficult to remove and can destroy the effectiveness of the stone. These metal shavings which are captured by the hone 11 do not present a problem because after each patient has been treated, the hone 11 can be scrubbed and ultrasonically cleaned to remove these shavings 45. Entrapment of these metal filings by the hone 11 prevents them from being introduced into the operative field. Because of impervious characteristics of hone 11, these shavings 45 can be routinely removed by scrubbing and ultrasonic cleaning.

The present invention avoids these problems because of the impervious nature of the hone which can be subjected to intense scrubbing and ultrasonic cleaning to remove this metal fouling. Since the slivers of metal 45 are trapped in the surface of the hone 11, and since the hone is strong enough to withstand intense scrubbing and ultrasonic cleaning, the metal chips 45 will be completely removed from the stone each time it is cleaned for reuse. Thus, the slivers 45 will not remain in the hone and destroy its effectiveness. Further, the slivers 45 will be removed so that they will not be transferred to the patient's mouth in future surgical or periodontal treatment.

Thus, it will be apparent that the current invention involves producing a ceramic hone 11 which consists of a mixture of aluminum oxide and magnesium oxide with a densifying agent if desired. The aluminum oxide is exposed to fusing temperatures in the range of 1450 to 1750 degrees F. in order to fuse the particles 34 to provide a strong, impervious ceramic block 11. The magnesium oxide, as previously indicated, is included in the mixture of abrasive aluminum oxide particles to inhibit crystal growth. It is desirable to keep the particle size 34 in the 0.5 micron to 8.5 micron size range in order to provide particles of optimum size for polishing. The fused particles 34 which are separated in voids between the particles 34 by the densifying agent 36 is then polished to produce flat surfaces which provide the cutting edges 40 characteristic of the present invention. The elongated flat surface 16 as illustrated in FIGS. 1 and 1a or flat surface 33 illustrated in FIG. 2 of the drawings is the surface which is polished to produce a flat uniform surface for sharpening one part of curette 18.

Elongated rounded edge 17 and elongated curved edge 31 of FIG. 4 of the drawings is also polished to produce the same effect as the polishing on flat surface 16. The edge 17 provides the surface used to sharpen the curved surfaces of the curette to provide a meticulously sharp edge 21.

Where a hone 11 or 26 having surfaces of differing grades of coarseness might be desired, the individual blocks 12 and 13 or blocks 27 and 28 might be treated differently. For example, block 12 could be prepared and polished in accordance with teachings of the present invention. Block 13, however, might simply be a block of particulate aluminum oxide abrasive material prepared in accordance with the present invention but with no polished surface. In this case, block 13 would have the appearance of the fused particles illustrated in FIG. 5 but with the tops 38 left intact without polishing. Such a ceramic hone block 13 will rapidly remove metal from a steel curette surface. It will also produce relatively large serrations, with the result that the sharpening process will require the use of block 12 in order to put the final finishing sharpness on the curette to produce an effective keen edge 21.

To produce a hone 11 which has both fine and coarse blocks involves a selection of attributes for the individual blocks 12 and 13 to produce fine and coarse surfaces, respectively. The first step in that process includes combining or mixing particulate aluminum oxide abrasive with magnesium oxide. A preferred mixture includes about 96% to about 99.9% aluminum oxide. Densifying agents may be added if desired.

Next, the mixture is shaped to form elongated blocks. The elongated blocks can be either in the shape indicated by block 12, which is essentially rectangular in shape and cross-section, or it may be a block in the shape illustrated in FIG. 4 of the drawings, which is essentially a block 27 which is triangular in cross-section. The shaping process can either occur by extruding the prepared mixtures to produce an extruded length of material of the length desired in the finished hone or the mixture can be molded in a well understood molding process to produce blocks of desired length and shape. The extrusion and molding are carried out using well understood techniques. Each technique exposes the mixture to high pressures which compact the mixture and increases the density of the block. An important attribute of the shaping step is the incorporation of at least one curved or rounded elongated edge 17 on the block. The radius R of curvature is within the limits set forth herein.

After the block has been shaped, the blocks are then ready to be subjected to elevated temperatures in a kiln in order to fuse the aluminum oxide particles 34. The kiln heating takes place within a temperature range of about 1450 degrees Centigrade to about 1750 degrees Centigrade. The preferred fusion temperature is in the range of 1550 degrees Centigrade to about 1650 degrees Centigrade.

After the blocks are heat treated they are then inspected for quality of the blocks. In some cases where the extrusion or the molding is imprecise, the blocks may contain small "flashings." "Flashings" are seams, projections and other slight extrusions or molding imperfections which are present at the edges of the blocks and are connected to the blocks in a very fragile way. Flashings will tend to dull the sharp edge of the dental instruments if they are not removed. Flashing can be removed from the individual blocks by tumbling for a period of time in the presence of a standard tumbling compound designed to remove such flashings. Tumbling will produce a fine quality block with definite sharp edges which will not dull dental cutting implements.

After the tumbling step is completed, the blocks can, as an optional matter, be lapped if necessary. Lapping is a machining process used to true the surface of the blocks. Lapping merely takes prominent features out of the surface 16 of the block 12 and produces a surface which is as true as possible without noticeable indentations, grooves, valleys or similar irregularities on the surface of the hone. In present day extrusion and molding processes, the techniques employed are usually sufficiently precise that lapping is not a necessary step in the production of a hone according to the present invention.

The next step in the process of producing a hone according to the present invention is the single most important step in the process and involves polishing. In this step, as previously explained, the exposed tops 38 of aluminum oxide abrasive particles which are exposed along the flat elongated surface 16 and the curved elongated edge 17 are cut with a polishing wheel or machine in order to flatten the tops of the particles 34 as illustrated in FIG. 5 of the drawings. As indicated, this polishing process produces a polished flat surface 30 which intersects with irregular sides 35 of the particles 34 to produce a cutting edge 40 on each of the aluminum oxide particles which is exposed on surfaces 16 and edge 17 or the corresponding surfaces of the stones illustrated in the other figures of the drawings. This polishing step is carried out by using diamond polishing wheels or diamond polishing compound to cut the tops 38 from the particles to produce the flat surface 30. With this step completed, a hone has been formed which has a good abrasive action and provides a hone capable of producing an extremely fine, sharp edge on a curette.

If a hone 11 is to have a fine surface produced according to the present invention combined with a block 13 of more coarse texture, then the individual blocks 12 and 13 must be joined to form a single unit. The individual blocks 12 and 13 can be joined as indicated in FIG. 1 of the drawings along joint 14 by application of an adhesive. The adhesive should be capable of withstanding autoclave temperatures and pressures is preferably a thermal setting epoxy resin which has a setting temperature in the range of about 240 degrees F. to about 260 degrees F. for approximately 40 minutes. Such a thermal setting epoxy resin found to be satisfactory for joining blocks of ceramic material is one made by Minnesota Mining and Manufacturing, Co. and is sold under the trademark "ScotchWeld No. 2214".

Epoxy thermal setting adhesive is applied to the surfaces of the blocks 12 and 13 in the case of hone 11 and then the block is baked at a temperature of 240 degrees Fahrenheit to about 260 degrees Fahrenheit for about 40 minutes in order to set the adhesive. When the adhesive is finally set, the result is a hone 11 which is capable of many years of use to produce fine quality cutting edges on curved dental implements. Such a hone 11 is also capable of being subjected to many cycles of ultrasonic cleaning and autoclave sterilization procedures without breaking down under such use. The hone may be vigorously scrubbed without damage.

This ceramic-based sharpening hone needs no liquid for lubricating the surface for proper sharpening of dental instruments. Many, many sharpening cycles can be performed on the hone with equal effectiveness. The hone captures small shavings 45 of metal from the surface 23 of the curette so that the shavings will not be transferred by the sharpened curette to the patient's mouth.

Because the hone 11 is a highly fused impervious ceramic, the abrasive particles 34 will not be given up on the surface of the hone as it is being used by the clinician in sharpening the stainless steel curettes. This is the reason hone 11 made according to the present invention does not require a lubricating agent. Because the particles 34 are not given up during the sharpening process, the surface of the hone 11 also remains true and does not develop valleys and groves which hinder the sharpening process.

Because the aluminum oxide particles 34 used to make up the hone 11 are much harder than the steel encountered in a curette, the particles 34 will not be worn and consequently the edge 40 produced by the flat polished surface 30 will not give up its cutting characteristics.

Figure 7:
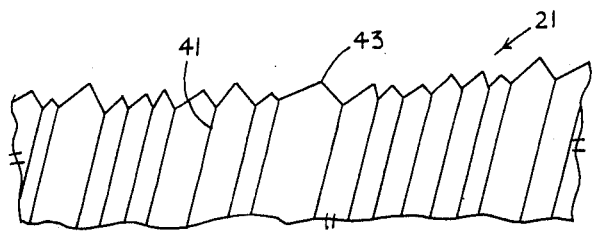
FIG. 7 is an enlarged fractional view of an edge of a dental curette taken along line 7—7 of FIG. 6 illustrating serrations and teeth formed in the edge of a sharpened dental curette.
Figure 8:
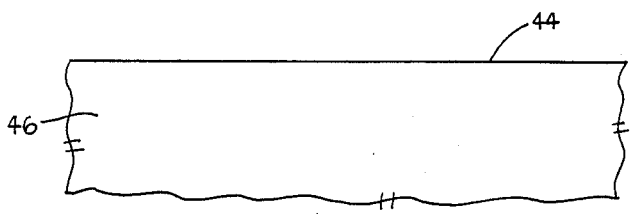
FIG. 8 is an enlarged fractional view of the edge of a dental curette shown in FIG. 7. After sharpening with a hone according to the present invention.

A demonstration of the effectiveness of a hone of the indicated characteristics and made according to the indicated process can be explained by reference to FIGS. 7 and 8 of the drawings. Prior art stones tend to "gouge" and furrow the surface of fine steel curettes to produce serrations in the surface being sharpened. These serrations are illustrated by numeral 41 in FIGS. 6 and 7 of the drawings. These serrations are actually groves which are cut out of the side surface 22 and face surface 23 of the curette. These serrations 41 on either side of the cutting edge 21 converge at the cutting edge 21. At this conversion, the serrations come together to produce a very ragged edge which is illustrated by the saw-tooth appearance of the surface generally designated by edge 21. Edge 21, as is apparent, is composed essentially of series of irregular teeth. This could be characterized as a rake-like surface or a saw-tooth surface. This produces a rough surface on the tooth and removes excess to structure.

These teeth 43 are of varying strength and sharpness and accordingly will vary in their ability to withstand the cutting necessary to remove cementum and dentin from the surface of a human tooth during a periodontal root planing procedure. These teeth 43 are weak since they are not supported on either side by substantial material in the cutting edge 21. Consequently, the teeth will tend to break or become bent. Whether the teeth 43 bend or break, nevertheless the result is a curette which becomes dull very quickly and needs resharpening. This resharpening, if done on prior art stones, removes excess metal and will merely produce additional such teeth 43, with the result that expensive dental cutting instruments will need to be sharpened so frequently that the implement is rapidly used up and will need to be discarded.

If the practitioner sharpening the particular curette 18 uses a common stone which does not have a curved surface to accommodate the face of the curette, he will not be able to remove the serrations that were put on the face of the curette when it was manufactured at the factory. These serrations often run parallel to the working edge 21 as illustrated by serration 42 of the drawings. These serrations 42, if parallel to the edge, tend to weaken the base of the sharp edge 21 with the result that it is possible for an entire section of the cutting edge 21 to break off or bend out of alignment. In either case, the cutting ability of the dental curette 18 is seriously impaired with the need to remove a large amount of metal in order to resharpen the instrument. This greatly reduces the life of the curette.

A dental hone 11 made according to the indicated composition of characteristics and with the indicated process will produce a stone which does not become weak when sterilized in autoclaves and cleaned in ultrasonic devices. The result of using a ceramic hone according to this invention with the indicated characteristics will produce a sharpened edge which is more characteristic of the smooth straight line illustrated by edge 44 in FIG. 8 of the drawings. In such an edge 44, the serrations have been removed from the sharpened surface 46 by cutting edge 40 so that no serrations weaken the base of the edge 44. Edge 44 becomes a continuous straight line with no weak teeth which can be bent out of alignment, broken or otherwise damaged. The result is a sharp edge 44 which has a great deal of strength and can therefore withstand the high pressures necessary to cut through cementum and tooth dentin to provide an effective and efficient root planing procedure.

Further, an edge such as edge 44 will not become dull nearly as quickly, thus reducing the need for repeated sharpening of the edge. Reduction of the number of sharpening procedures dramatically extends the life of expensive dental curettes. A meticulously sharp instrument that becomes dull requires removal of far less metal from the instrument to resharpen it. Since the curettes are designed to have a curved cutting surface 21 which accommodates the curved surface of a human tooth root, the curved edges 17 and 31 of hones 11 and 26, respectively, will permit sharpening of such a curved surface across these curved honing edges with the most efficient generation of a smooth surface 44. As is well known in the art of sharpening steel instruments, a hone should be drawn across the surface being sharpened perpendicular to the cutting edge in order to produce a fine sharp edge which is as uniform and straight as possible. The curved edges 17 and 31 permit perpendicular stroking of the curette edge 21 along this curved surface and thus promote this efficient and effective sharpening procedure to produce the straight strong tooth-free edge illustrated in FIG. 8 of the drawings.

The above described hone for use in connection with sharpening of dental cutting instruments and the method of producing such a hone is only a specific illustration of a preferred embodiment of such invention. Variations of the above method and attributes may be made without departing from the spirit and scope of the invention.

What is claimed is:

1. A curette hone which comprises a block having an elongated flat surface forming elongated edges, said block comprising a uniform composition of fused aluminum oxide abrasive and magnesium oxide, the amount of aluminum oxide present in said composition being greater than about 83%, said aluminum oxide being in particle form, with the particles being irregular in shape and in a size range from about 0.5 microns to about 8.5 microns, at least one elongated edge of said block having a rounded surface with a radius of about 1/32 inch to about 3/32 inch, aluminum oxide particles being exposed on the flat surface and on the rounded edge of said block and said exposed particles having a flat polished surface intersecting irregular sides of said exposed particles to form a cutting edge on each such polished particle to provide the abrasive action of large abrasive particles and the fine honing qualities of small abrasive particles.

2. A hone in accordance with claim 1 in which said aluminum oxide in said uniform composition is in the range of about 96% to about 99.9%.

3. A hone in accordance with claim 1 in which said uniform mixture includes a densifying agent.

4. A hone in accordance with claim 3 in which said densifying agent is selected from the group consisting of silicon oxide, ferrous oxide, sodium oxide, chromium oxide, potassium oxide, phosphorus oxide, barium oxide and calcium oxide.

5. A curette hone which comprises a first block and a second block with each block being elongated with a flat elongated surface forming elongated edges, said first and second blocks each comprising a uniform composition of fused aluminum oxide abrasive; magnesium oxide and a densifying agent selected from the group consisting of silicon oxide, ferrous oxide, sodium oxide, chromium oxide, potassium oxide, phosphorus oxide, barium oxide, and calcium oxide, the amount of aluminum oxide present in said composition being at least 83%, said aluminum oxide being in particle form, with the particles being irregular in shape and in a size range from about 0.5 microns to about 8.5 microns, at least one elongated edge of each of said first and second blocks forming a rounded surface with a radius of about 1/32 inch to about 3/32 inch, the aluminum oxide particles being exposed on the surface of said rounded edge and flat elongated surface of said first block having a flat polished surface intersecting irregular sides of said exposed particles to form a cutting edge on each such polished particle, and said first and second blocks being joined by a bonding agent, said first and second blocks being joined to expose each of said curved surfaces for sharpening a curved edge of a dental curette.

6. A hone in accordance with claim 5 in which said bonding agent is an epoxy resin.

7. A hone in accordance with claim 6 in which said bonding agent is a thermosetting epoxy resin.

8. A hone in accordance with claim 7 in which said thermosetting resin has a setting temperature of about 240° F. to about 260° F.

9. A hone in accordance with claim 5 in which said first and second blocks each have a cross-sectional shape of a triangle and in which said blocks are joined by said bonding agent with said surface of each of said first and second blocks being located at opposite extremes of the cross-section of the joined blocks.

10. A hone in accordance with claim 5 in which said first and second blocks each have a cross-sectional shape of a square and in which said blocks are joined along a surface of each block by said bonding agent to form a joint with said rounded surface of each of said first and second blocks being located on each block out of contact with said joint.

11. A hone in accordance with claim 5 in which said first and second blocks each have a cross-sectional shape of a rectangle and in which said blocks are joined along a surface of each block by said bonding agent to form a joint with said rounded surface of each of said first and second blocks being located on each block out of contact with said joint.

12. A curette hone which comprises a first block and a second block with each block being elongated with a flat elongated surface forming elongated edges, said first and second blocks each comprising a uniform composition of fused aluminum oxide abrasive and magnesium oxide, the amount of aluminum oxide present in said composition being at least 96% said aluminum oxide being in particle form with the particles being irregular in shape and in a size range from about 0.5 microns to about 8.5 microns, at least one elongated edge of each of said first and second blocks forming a rounded surface with a radius of about 1/32 inch to about 3/32 inch, the aluminum oxide particles being exposed on the surface of said rounded edge and flat elongated surface of said first block having a flat polished surface intersecting irregular sides of said exposed particles to form a cutting edge on each such polished particle, and said first and second blocks being joined by a bonding agent, said first and second blocks being joined to expose each of said curved surfaces for sharpening a curved edge of a dental curette.

13. A curette hone which comprises a first block and a second block with each block being elongated with a flat elongated surface forming elongated edges, said first and second blocks each comprising a uniform composition of fused aluminum oxide abrasive; magnesium oxide and a densifying agent selected from the group consisting of silicon oxide, ferrous oxide, sodium oxide, chromium oxide, potassium oxide, phosphorus oxide, barium oxide, and calcium oxide, the amount of aluminum oxide present in said composition being at least 96% in said first block and at least 83% in said second block, said aluminum oxide being in particle form with the particles being irregular in shape and in a size range from about 0.5 microns to about 8.5 microns, at least one elongated edge of each of said first and second blocks forming a rounded surface with a radius of about 1/32 inch to about 3/32 inches, the aluminum oxide particles being exposed on the surface of said rounded edge and flat elongated surface of said first block having a flat polished surface intersecting irregular sides of said exposed particles to form a cutting edge on each such polished particle, and said first and second blocks being joined by a bonding agent, said first and second blocks being joined to expose each of said curved surfaces for sharpening a curved surface of a dental curette.

14. A method of making a hone for sharpening a curette having a curved cutting surface which comprises the steps of:
(a) Combining 83% or greater particulate aluminum oxide having particles of irregular size with magnesium oxide to form a uniform mixture,
(b) Shaping said uniform mixture into an elongated block having an elongated flat surface and a rounded edge having a radius of from about 1/32 inch to about 3/32 inch,
(c) Heating said block to a temperature of about 1450° C. to about 1750° C. to fuse the particles of aluminum oxide, and then
(d) Polishing said flat surface and rounded edge to produce a polished surface on the aluminum oxide particles exposed on said flat surface and rounded edge to form a cutting edge on each particle at the intersection of the polished surface and the sides of said irregular particles.

15. A method of making a hone for sharpening a curette having a curved cutting surface which comprises the steps of:
(a) Combining 83% or greater particulate aluminum oxide having particles of irregular size with magnesium oxide to form a uniform mixture,
(b) Shaping said uniform mixture into an elongated block having an elongated flat surface and a rounded edge having a radius of from about 1/32 inch to about 3/32 inch,
(c) Heating said block to a temperature of about 1450° C. to about 1750° C. to fuse the particles of aluminum oxide,
(d) Tumbling said block in the presence of a tumbling agent to remove irregularities from the surface and edges of said block, and then
(e) Polishing said flat surface and rounded edge to produce a polished surface on aluminum oxide particles exposed on said flat surface and rounded edge to form a cutting edge on each particle at the intersection of the polished surface and the sides of said irregular particles.

16. A method in accordance with claim 15 which further includes the step of lapping the said elongated flat surface and said rounded edge after tumbling and before polishing to remove irregularities in said flat surface and said rounded surface.

17. A method of making a hone for sharpening a curette having a curved cutting surface which comprises the steps of:
(a) Combining 83% or greater particulate aluminum oxide having particles of irregular size with magnesium oxide to form a first uniform mixture,
(b) Combining 83% or greater particulate aluminum oxide having particles of irregular size with magnesium oxide to form a second uniform mixture,
(c) Shaping said first uniform mixture into an elongated block having a elongated flat surface and a rounded edge having a radius of from about 1/32 inch to about 3/32 inch,
(d) Shaping said second uniform mixture into an elongated block having an elongated flat surface and a rounded edge having a radius of from about 1/32 inch to about 3/32 inch, (e) Heating said first and second blocks to a temperature of about 1450° C. to about 1750° C. to fuse the particles of aluminum oxide,
(f) Polishing said flat surfaces and rounded edge of said first block to produce a polished surface on aluminum oxide particles exposed on said flat surface and rounded edge of said first block to form a cutting edge on each particle at the intersection of the polished surface and the sides of said irregular particles, and then
(g) Bonding said first and second blocks with a bonding agent to form a hone having blocks of differing sharpening coarseness for sharpening dental curettes.

18. A method in accordance with claim 17 in which said bonding agent is a thermosetting epoxy resin having a setting temperature in the range of about 240° F. to about 260° F. and which further includes the step of heating the bonding agent to the said temperature range for approximately 40 minutes to set the epoxy resin.

19. A method in accordance with claim 17 which further includes the step of lapping the said elongated flat surface and said rounded edge after tumbling and before polishing to remove irregularities in said flat surface and said rounded surface.

20. A hone which comprises a block having a honing surface and composed of an impervious ceramic abrasive selected from the group consisting essentially of aluminum oxide and silicon carbide and further comprising a growth inhibiting agent, magnesium oxide, said honing surface formed of an abrasive composed of fused abrasive particles, the particles on said honing surface having a polished surface to form cutting edges on the abrasive particles for sharpening instruments.

21. A hone in accordance with claim 20 in which said fused particles have a particle size of approximately 0.5 to 8.5 microns.

22. A hone in accordance with claim 20 in which said block is composed of a composition of fused abrasive and a crystal growth inhibiting agent to prevent individual abrasive particles from growing to larger particles.

23. A hone in accordance with claim 22 in which said composition includes an amount of abrasive in excess of 83%.

24. A hone in accordance with claim 20 which further includes a densifying agent.

25. A hone in accordance with claim 24 in which said densifying agent is selected from the group consisting of silicon oxide, ferrous oxide, sodium oxide, chromium oxide, potassium oxide, phosphorus oxide, barium oxide and calcium oxide.

26. A hone for sharpening instruments which comprises a block having a honing surface and composed of an impervious ceramic abrasive composition comprising 83% or greater aluminum oxide or silicon carbide with magnesium oxide, said honing surface formed of an abrasive composed of fused particles having irregular shapes and outer surfaces, the particles on said honing surface having a polished surface to form cutting edges at the intersection of said polished surface and said outer surfaces of the abrasive particles for sharpening instruments by slicing small slivers of material from the instrument as the instrument is drawn along said honing surface.

27. A method of making a home having a honing surface for sharpening instruments which comprises the steps of:
(a) Shaping 83% or greater aluminum oxide or silicon carbide abrasive particles with magnesium oxide into an elongated block having individual abrasive particles exposed on said honing surface,
(b) Heating said block to a temperature of about 1450° C. to about 1750° C. to fuse the abrasive particles, said fusing being sufficiently strong to prevent the individual particles from being dislodged when the hone is used to sharpen an instrument, and then
(c) Polishing the individual abrasive particles exposed on said honing surface to produce polished surfaces on said individual particles to form a cutting edge on each abrasive particle at the intersection of the polished surface and sides of each of the said abrasive particles.

28. A method in accordance with claim 27 which further includes the step of combining abrasive particles in a uniform mixture with a crystal growth inhibiting agent prior to shaping to prevent individual abrasive particles from growing to larger particles.

29. A method in accordance with claim 27 in which said particulate abrasive is aluminum oxide.

30. A method in accordance with claim 27 in which said growth inhibiting agent is magnesium oxide.

31. A method in accordance with claim 27 which further includes the step of lapping the honing surface of the hone before polishing to remove irregularities in the honing surface.

32. A hone which comprises a block having a curved honing surface and composed of an impervious ceramic abrasive selected from the group consisting essentially of aluminum oxide and silicon carbide and further comprising a growth inhibiting agent magnesium oxide, said curved honing surface formed of an abrasive composed of fused abrasive particles, the particles on said curved honing surface having a polished surface to form cutting edges on the abrasive particles for sharpening instruments.

33. A hone in accordance with claim 32 in which said curved honing surface has a radius of approximately 1/32 to about 3/32.

34. A hone in accordance with claim 32 in which said block is composed of a composition of abrasive and a crystal growth inhibiting agent to prevent individual abrasive particles from growing to larger particles and in which said fused particles have a particle size of approximately 0.5 to 8.5 microns.

35. A method of making a hone having a curved honing surface for sharpening instruments which comprises the steps of:
(a) Shaping 83% or greater aluminum oxide or silicon carbide abrasive particles with magnesium into an elongated block having at least one curved honing surface and with individual abrasive particles exposed on said curved honing surface,
(b) Heating said block to a temperature of about 1450° C. to about 1750° C. to fuse the abrasive particles, said fusing being sufficiently strong to prevent the individual particles from being dislodged when the hone is used to sharpen an instrument, and then
(c) Polishing the individual abrasive particles exposed on said curved honing surface to produce polished surfaces on said individual particles to form a cutting edge on each particle at the intersection of the polished surface and sides of each of the said abrasive particles.

36. A method in accordance with claim 35 which further includes the step of lapping the curved honing surface of the hone before polishing to remove irregularities in the curved honing surface.

37. A method in accordance with claim 35 which further includes the step of combining abrasive particles in a uniform mixture with a crystal growth inhibiting agent prior to shaping to prevent individual abrasive particles from growing to larger particles, said particles having a particle size limited to approximately 0.5 to 8.5 microns.

* * * * *

UNITED STATES PATENT AND TRADEMARK OFFICE
CERTIFICATE OF CORRECTION

PATENT NO. : 4,838,899
DATED : June 13, 1989
INVENTOR(S) : Edward J. Bifulk

It is certified that error appears in the above—identified patent and that said Letters Patent is hereby corrected as shown below:

On the title page, please correct the Inventor's name which has been incorrectly spelled as "Bifuk" to --Bifulk-- both in the heading of the title page of the patent and after [76] Inventor.

Signed and Sealed this

Thirtieth Day of July, 1991

Attest:

HARRY F. MANBECK, JR.

Attesting Officer

Commissioner of Patents and Trademarks